US008580514B2

(12) United States Patent
Tzean et al.

(10) Patent No.: US 8,580,514 B2
(45) Date of Patent: Nov. 12, 2013

(54) **MICROCHIP FOR IDENTIFYING *PHELLINUS* SPECIES AND THE METHOD THEREOF**

(75) Inventors: Shean-Shong Tzean, Taipei (TW); Po-Yao Shu, Taipei (TW); Yuh Tzean, Taipei (TW)

(73) Assignee: National Taiwan University, Taipei (TW)

( * ) Notice: Subject to any disclaimer, the term of this patent is extended or adjusted under 35 U.S.C. 154(b) by 500 days.

(21) Appl. No.: 12/614,119

(22) Filed: Nov. 6, 2009

(65) Prior Publication Data

US 2011/0111970 A1    May 12, 2011

(51) Int. Cl.
*C12Q 1/68* (2006.01)
*C12M 1/34* (2006.01)
*C07H 21/04* (2006.01)

(52) U.S. Cl.
USPC ..... 435/6.15; 435/6.11; 435/6.12; 435/287.2; 536/23.1; 536/24.3; 536/24.33

(58) Field of Classification Search
None
See application file for complete search history.

(56) References Cited

U.S. PATENT DOCUMENTS 6,713,257 B2 * 3/2004 Shoemaker et al. ......... 435/6.13

FOREIGN PATENT DOCUMENTS

WO    WO 9947706 A1 * 9/1999

OTHER PUBLICATIONS

Park, D. et al. Mycobiology 29(1):7-10 (2001).*
Leinberger, D.M. et al. J. Clin. Microbiol. 43(10):4943 (Oct. 2005).*
Klaassen, C.H. et al. J. Clin. Microbiol. 42(5):2152 (May 2004).*
Yin, H. et al. Journal of Microbiological Methods 70:165 (Apr. 2007).*
GenBank Accession No. AF251438, Park et al, Oct. 2000.*

* cited by examiner

*Primary Examiner* — Diana Johannsen
(74) *Attorney, Agent, or Firm* — WPAT, P.C.; Anthony King

(57) ABSTRACT

The developed oligonucleotide microchip for simultaneous, rapid identification of multiple crucial forest *Phellinus* pathogens was based on the DIG or biotin-labeled specific probes derived form ribosomal DNA genes (ITS1-5.8S-ITS2), by using reverse-dot hybridization. The chip can precisely and accurately identify and diagnose seventeen *Phellinus* species, including notorious hardwood and conifer tree killer, *P. noxius* and *P. weirii*, with a sensitivity of 1 pg DNA/μl on Nylon membrane, and 100 fg DNA/μl on plastic chip, respectively. Verification and identification of forest *Phellinus* pathogens infested authentic samples or voucher specimens can be accomplished within 7 hr.

15 Claims, 10 Drawing Sheets

| Phapi | Phces | Phgil | PM | Phlin | Phine |
|-------|-------|-------|----|-------|-------|
| Phlav | Phmell| Phmem | PM | Phnox | Phpin |
| Phque | Phrib | Phign | PM | Phfor | Phpac |
| PM    | PM    | PM    | PM | PM    | PM    |
| PC    | HC    | NC    | PM | Phtor | Phwei |

SEQUENCE LISTING

```
<160> NUMBER OF SEQ ID NOS: 21

<210> SEQ ID NO 1
<211> LENGTH: 53
<212> TYPE: DNA
<213> ORGANISM: Artificial sequence
<220> FEATURE:
<223> OTHER INFORMATION: Probe for identifying Phellinus apiahynus

<400> SEQUENCE: 1
gtcttgtccc ctcttttcat aggagggggg ggaccagtct ttcaagctgg tat        53

<210> SEQ ID NO 2
<211> LENGTH: 53
<212> TYPE: DNA
<213> ORGANISM: Artificial sequence
<220> FEATURE:
<223> OTHER INFORMATION: Probe for identifying Phellinus cesatii

<400> SEQUENCE: 2
taatagtatt gtggtggcca tttgctgtta ttcattgtta gaagcgggta acc        53
```

```
<210> SEQ ID NO 3
<211> LENGTH: 53
<212> TYPE: DNA
<213> ORGANISM: Artificial sequence
<220> FEATURE:
<223> OTHER INFORMATION: Probe for identifying Phellinus gilvus

<400> SEQUENCE: 3
ggattgaaag tcgaggcgca agtcttgact ggagagaaac ctttctacgt ttt        53

<210> SEQ ID NO 4
<211> LENGTH: 53
<212> TYPE: DNA
<213> ORGANISM: Artificial sequence
<220> FEATURE:
<223> OTHER INFORMATION: Probe for identifying Phellinus linteus

<400> SEQUENCE: 4
agagtcgaag ctggagtagt ctctgtaatc gaaacgggct tttgaagtat gct        53

<210> SEQ ID NO 5
<211> LENGTH: 28
<212> TYPE: DNA
<213> ORGANISM: Artificial sequence
<220> FEATURE:
<223> OTHER INFORMATION: Probe for identifying Phellinus inermis

<400> SEQUENCE: 5
gttagtaaaa ggggcaagga gtaatcct                                     28

<210> SEQ ID NO 6
<211> LENGTH: 53
<212> TYPE: DNA
<213> ORGANISM: Artificial sequence
<220> FEATURE:
<223> OTHER INFORMATION: Probe for identifying Phellinus lavegatus

<400> SEQUENCE: 6
ttgggcgttt aggacggagt aatgagtaga aaggaggtgt aatgcttcca ttt        53

<210> SEQ ID NO 7
<211> LENGTH: 53
<212> TYPE: DNA
<213> ORGANISM: Artificial sequence
<220> FEATURE:
<223> OTHER INFORMATION: Probe for identifying Phellinus melleoporus

<400> SEQUENCE: 7
tcaaacttaa ctcggttgaa gtgggggag gaacagtgca aggaggtggt gaa         53

<210> SEQ ID NO 8
<211> LENGTH: 53
<212> TYPE: DNA
<213> ORGANISM: Artificial sequence
<220> FEATURE:
<223> OTHER INFORMATION: Probe for identifying Phellinus membraneceus

<400> SEQUENCE: 8
aggtcggtga aagatataag tgtctctgac gcttgtattg gaagccttcc tat        53

<210> SEQ ID NO 9
<211> LENGTH: 53
<212> TYPE: DNA
<213> ORGANISM: Artificial sequence
<220> FEATURE:
<223> OTHER INFORMATION: Probe for identifying Phellinus noxius
```

```
<400> SEQUENCE: 9
ctgaagagag agagggagag ggagagtggt ttattcgttt attcatttat tcg          53

<210> SEQ ID NO 10
<211> LENGTH: 53
<212> TYPE: DNA
<213> ORGANISM: Artificial sequence
<220> FEATURE:
<223> OTHER INFORMATION: Probe for identifying Phellinus pini

<400> SEQUENCE: 10
gccgtcgggg ttgactttgt tagtagtgtt tcgacgcgaa agcatacggt cgg          53

<210> SEQ ID NO 11
<211> LENGTH: 53
<212> TYPE: DNA
<213> ORGANISM: Artificial sequence
<220> FEATURE:
<223> OTHER INFORMATION: Probe for identifying Phellinus quercinus

<400> SEQUENCE: 11
attgctacaa gtatgttaat aaggcgaacg cactcttttc ggtgttacta gct          53

<210> SEQ ID NO 12
<211> LENGTH: 53
<212> TYPE: DNA
<213> ORGANISM: Artificial sequence
<220> FEATURE:
<223> OTHER INFORMATION: Probe for identifying Phellinus ribis

<400> SEQUENCE: 12
acgcaagtga gtcgtcagtt ccctaagtt gggagtgact tgatttgctt cgt           53

<210> SEQ ID NO 13
<211> LENGTH: 53
<212> TYPE: DNA
<213> ORGANISM: Artificial sequence
<220> FEATURE:
<223> OTHER INFORMATION: Probe for identifying Phellinus igniarius

<400> SEQUENCE: 13
agttggcggt tagtagtcgt aaggcgaaca cttgtcggcg aacacttcaa tat          53

<210> SEQ ID NO 14
<211> LENGTH: 53
<212> TYPE: DNA
<213> ORGANISM: Artificial sequence
<220> FEATURE:
<223> OTHER INFORMATION: Probe for identifying Phellinus formosanus

<400> SEQUENCE: 14
ggggcgagac ctttgagttc gaagacagta gttctttttg caaatgtgag ggc          53

<210> SEQ ID NO 15
<211> LENGTH: 53
<212> TYPE: DNA
<213> ORGANISM: Artificial sequence
<220> FEATURE:
<223> OTHER INFORMATION: Probe for identifying Phellinus pachyphloens

<400> SEQUENCE: 15
aatctctggc cattggtgtc tttcattaga cgtcgacgtg cctttaactt tga          53

<210> SEQ ID NO 16
<211> LENGTH: 53
```

-continued

```
<212> TYPE: DNA
<213> ORGANISM: Artificial sequence
<220> FEATURE:
<223> OTHER INFORMATION: Probe for identifying Phellinus torulosus

<400> SEQUENCE: 16
cgtatgttgg gtcgatggaa ggtaaagctt tacggcggca tcttctttag gtc          53

<210> SEQ ID NO 17
<211> LENGTH: 50
<212> TYPE: DNA
<213> ORGANISM: Artificial sequence
<220> FEATURE:
<223> OTHER INFORMATION: Probe for identifying Phellinus weirii

<400> SEQUENCE: 17
gcacttttcg aagtctgtcg tcggctccca tttggagcag ctggaggttt              50

<210> SEQ ID NO 18
<211> LENGTH: 29
<212> TYPE: DNA
<213> ORGANISM: Artificial sequence
<220> FEATURE:
<223> OTHER INFORMATION: ITS5e primer

<400> SEQUENCE: 18
ttagaggaag taaaagtcgt aacaaggtt                                     29

<210> SEQ ID NO 19
<211> LENGTH: 25
<212> TYPE: DNA
<213> ORGANISM: Artificial sequence
<220> FEATURE:
<223> OTHER INFORMATION: ITS4e primer

<400> SEQUENCE: 19
tcctccgctt attgatatgc ttaag                                         25

<210> SEQ ID NO 20
<211> LENGTH: 60
<212> TYPE: DNA
<213> ORGANISM: Artificial sequence
<220> FEATURE:
<223> OTHER INFORMATION: probe for positive control

<400> SEQUENCE: 20
attcactgaa ttctgcaatt cacattactt atcgcatttc gctgcgttct tcatcgatgc   60

<210> SEQ ID NO 21
<211> LENGTH: 55
<212> TYPE: DNA
<213> ORGANISM: Artificial sequence
<220> FEATURE:
<223> OTHER INFORMATION: probe for hybridization control

<400> SEQUENCE: 21
gctgtcattt tgggtactgc caccaaccac tctgccgatg ccatctccat caccc        55
```

MICROCHIP FOR IDENTIFYING *PHELLINUS* SPECIES AND THE METHOD THEREOF

BACKGROUND OF THE INVENTION

1. Field of the Invention

The present invention relates to a DNA microchip for identifying fungal species and a method thereof, in particular to a DNA microchip for identification of *Phellinus noxius* and allied species and a method thereof.

2. The Prior Arts

It has been known that there are about more than 80,000 species of fungi, approximately 8000 species of which are plant pathogens that cause various types of plant diseases in agriculture, horticulture and forestry. Some plant diseases even lead to famine and massive mortality of the forests. The issue of how to rapidly, precisely and sensitively identify fungal pathogens in order to take proper and effective measures for prevention and management in advance, reduce loss of life and property and promote social welfare is indeed of great urgency.

*Phellinus noxius*, a species of *Phellinus*, is particularly a notorious fungal pathogen that is considered as forests killer. The fungus infects and colonizes the roots and stem base of the forests and results in tissue degradation and decay and finally the whole plant is dried out. This has been extensively reported in Asia, Africa, Australia and New Zealand. It has been also reported a couple of decades, and particularly prevalent more recently in Taiwan, that at least 140 kinds of forests, including ornamental trees, fruit trees and forestation tree species, have been infected by the fungus, which leads to acute or chronic wilting or drying out, landscape destruction, economic loss and environmental safety. In addition, the other species of *Phellinus*, for example *Phellinus pini* and *Phellinus werii* belonging to the same genus but different species or *A. mellea* from the genus *Armillariella* or *A. ostoyae* from the genus *Armillaria*, were also reported in the USA, Canada, Australia, New Zealand and Europe to infect massive coniferous forests or broad-leaved forests, which causes poor growth, weakness, early defoliation, advanced blooming, decay, withering and top-over of the plants in windbreak and hence becomes an enormous restricted factor and a potential severe threat to forest management.

Traditionally, the diagnosis of plant diseases is carried out according to Koch's postulates, the process of which includes i) isolation and identification of pathogens from the lesion of the infected plants; ii) multiplication of the pathogens in vitro or in vivo; iii) back inoculation of the pathogens to healthy plants to generate the same disease with identical symptoms; iv) re-isolation and verification of the pathogens. This is a process of re-establishing and verifying the disease cycle. Accordingly, it is obvious that pathogenic identification is the main step in the diagnosis of plant diseases. The diagnosis in tradition principally depends on the features of the microscopic or macroscopic morphology, structure and sporogenesis of a pathogen. However, if anyone wants to correctly identify such diverse and structurally complicated fungi, besides familiarity with distinctions among various forms, to accept learning, education and training, also requires practical operation and experience accumulation over a long period of time and therefore a seriously burden. The dramatic progress in molecular biology in recent years, there is some significant progress, particularly with respect to systematic, phylogeny and identification of plant pathogens, for examples amplified DNA fragment length polymorphism (AFLP), rapid amplification of DNA polymorphism (RAPD), simple sequence repeat (SSR), selected characterized amplified region of DNA (SCAR), nano-magnetic bead polymerase chain reaction (NMB-PCR), multi-plex PCR and suspension microsphere-based array. However, there was no method available for a rapid identification of *Phellinus noxiusu* and closely related fungal pathogens until 2009, which do severely harm to the forests, so that domestic and foreign quarantine and inspection institutions are not capable of monitoring and rapidly and precisely identifying the fungal pathogens to curtail their accidental introduction. Furthermore, the early symptoms caused by the pathogens often vary with the habitat, growth and age of the plants and the infectious potential of the pathogens. Even the early symptoms are not so remarkable and therefore this makes an accurate diagnosis more difficult. If a rapid diagnosis and a precise identification can be performed in the early phase, this will become the essential factor for prevention of the occurrence and prevalence of such diseases in nursery, or tree species for forestation and selection of habitats. Consequently, the development of a rapid and precise technique for diagnosis and identification is becoming an urgent theme.

SUMMARY OF THE INVENTION

The internal transcribed spacer (ITS) of nuclear ribosomal DNA (rDNA) from all biological species has a highly tandem repeat sequence. The present invention provides the distinct oligonucleotide probes with the repeated sequence of an operon consisting of 18S, ITS1-5.8S-ITS2, 28S. ITS1 and ITS2 are the internal transcribed spacers spliced during transcription of rDNA to form rRNA (mRNA), and therefore do not have any function. They are also called pseudo-intron and have high variability. In contrast, the neighboring 5.8S, 18S and 18S rRNA possess a transcriptional function and therefore are more conservative and have low variability. Since rRNA (rDNA) has dual characteristics of variability and conservativeness, the difference in the sequences of rRNA (rDNA) can be used to explore the molecular phylogenetic relationship and the classification at various levels, for example intraspecies level, interspecies level, intergeneric level and above-genus level. Moreover, it can be used as objective reference. The present invention applied the rDNA difference sequence in combination with polymerase chain reaction (PCR) and reverse blot hybridization, or microchip to identify fungal species with close relationship.

The present invention is directed to digoxigenin (DIG) or biotin-labeled specific oligonucleotide probes based on universal primers to amplify, sequence, compare and analyze for accurate, sensitive identification of multiple crucial forest *Phellinus* pathogens. The present invention includes the use of a microarrayer to dot the specific oligonucleotide probes on a plastic chip or a nylon membrane to form a microchip in combination with PCR to amplify and label the target DNA of the forest *Phellinus* pathogens, and the subsequent reverse-dot hybridization. Therefore, the microchip can simultaneously, rapidly, and accurately identify and diagnose seventeen *Phellinus* species.

An object of the present invention is to provide a nucleic acid probe for identification of *Phellinus* species in relatives-relationship.

A further object of the present invention is to provide a microchip for identification of *Phellinus* species in relatives-relationship.

An another object of the present invention is to provide a method for identification of *Phellinus* species in relatives-relationship.

To fulfill the abovementioned purpose, the present invention provides an oligonucleotide probe, which is selected from the group consisting of: SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16 and SEQ ID NO:17. The above oligonucleotide probes used in this invention were listed in Table 2. The oligonucleotide probes of Table 2 are applied to identify *Phellinus* species i.e. *P. apiahynus, P. cesatii, P. gilvus, P. linteus, P. inrmis, P. laevigatus, P. melleoporus, P. membrance, P. noxius, P. pini, P. quercinus, P. ribis, P. formosanus, P. igniarius, P. pachyphloens, P. torulosus,* and *P. weirii,* as seen in Table 1.

A microchip for identifying *Phellinus* species is constructed using the seventeen oligonucleotide probes, wherein the substrate of the microchip is a nylon membrane, a plastic material or other suitable material, for example glass.

A further object of the present invention is to provide a method of detecting a *Phellinus* species by using the microchip of the present invention, which comprises:
(a) extracting DNA from a sample;
(b) amplifying an internal transcribed spacer (ITS) of a 18S-28S rDNA gene of the extracted DNA to obtain an amplification product;
(c) hybridizing the amplification product with the microchip as claimed in claim 1; and
(d) determining whether the amplification product detectably hybridize to the DNA probes of the microchip.

With hybridization result between the amplification product of the sample and the DNA probes, the present invention can identify a crucial *Phellinus* pathogen that infected the sample according to the position of the DNA probe corresponding to the seventeen *Phellinus* pathogens.

Efficiency of the Present Invention in Comparison with that of the Prior Art

The forest pathogens could be rapidly diagnosed and identified by using a microchip or probes according to the present invention, and the method disclosed in the present invention, which has the following advantages: i) high accuracy; ii) less time consumption and iii) easy handling, can provide nursery and seedlings early diagnosis, detection and certification, and for the affiliation of the domestic and foreign custom inspection and quarantine, including coniferous trees, broad leaf trees and seedlings. And also can be used in ecology monitoring, silviculture management and policy decisions.

The microchip according to the present invention can provide the diagnosis and detection of diseases, caused by fungal pathogens, in the root and stem regions of the trees in tree nurseries, parks, schools, road tree regions, resorts and forest districts and also a certificate for healthy seedlings. Additionally, it can provide basic information for policy making with respect to strengthening the screening of tree species for forestation, forest nursery and implementation of ecological preventive measures.

The present invention is further explained in the following embodiment illustration and examples. Those examples below should not, however, be considered to limit the scope of the invention, it is contemplated that modifications will readily occur to those skilled in the art, which modifications will be within the spirit of the invention and the scope of the appended claims.

BRIEF DESCRIPTION OF THE DRAWINGS

FIG. 3 (B) is a real object presentation of producing the microchip according to the present invention;

FIG. 6 (B) shows the test results on the sensitivity of the probes with respect to the plastic array, in comparing the sensitivity in gel in PCR.

DETAILED DESCRIPTION OF THE PREFERRED EMBODIMENT

To enable persons skilled in the art to better understand the aforementioned objective, features and advantages of the present invention, embodiments are quoted and explained in combination with attached figures as follows.

As used herein, the term "internal transcribed spacer (ITS)" and 5.8S refers to non-transcriptional and transcriptional domains of rRNA encoded by rDNA, in particular to the ITS1 region between 18S and 5.8 S and the ITS2 region between 5.8S and 28S and is often applied to identify diverse fungal species of the fungal genus.

The term "The fungal pathogens" refers to plant pathogenic fungi of *Phellinus* that cause plant diseases.

The term "oligonucleotide probe" refers to a small segment of single-stranded DNA (containing ten to several hundred bases), which is used to detect the complementary sequence.

The term "universal primers" refers to nucleic acid primers for rDNA between 18S and 28S, which can be generally used for diverse species of *Phellinus.*

The term "microchip" refers to a gene chip, also called a DNA microarray, which undergoes DNA sequence determination by hybridizing with a groups of probes with known sequence.

The term "nylon membrane chip" refers to the microchip formed by immobilizing nucleotide probes on the nylon membrane.

The term "plastic chip" refers to the microchip formed by immobilizing nucleotide probes on the plastic material.

EXAMPLE 1

Collection of Fungal Species for Experiment and Purified Culture

Figure 1A:
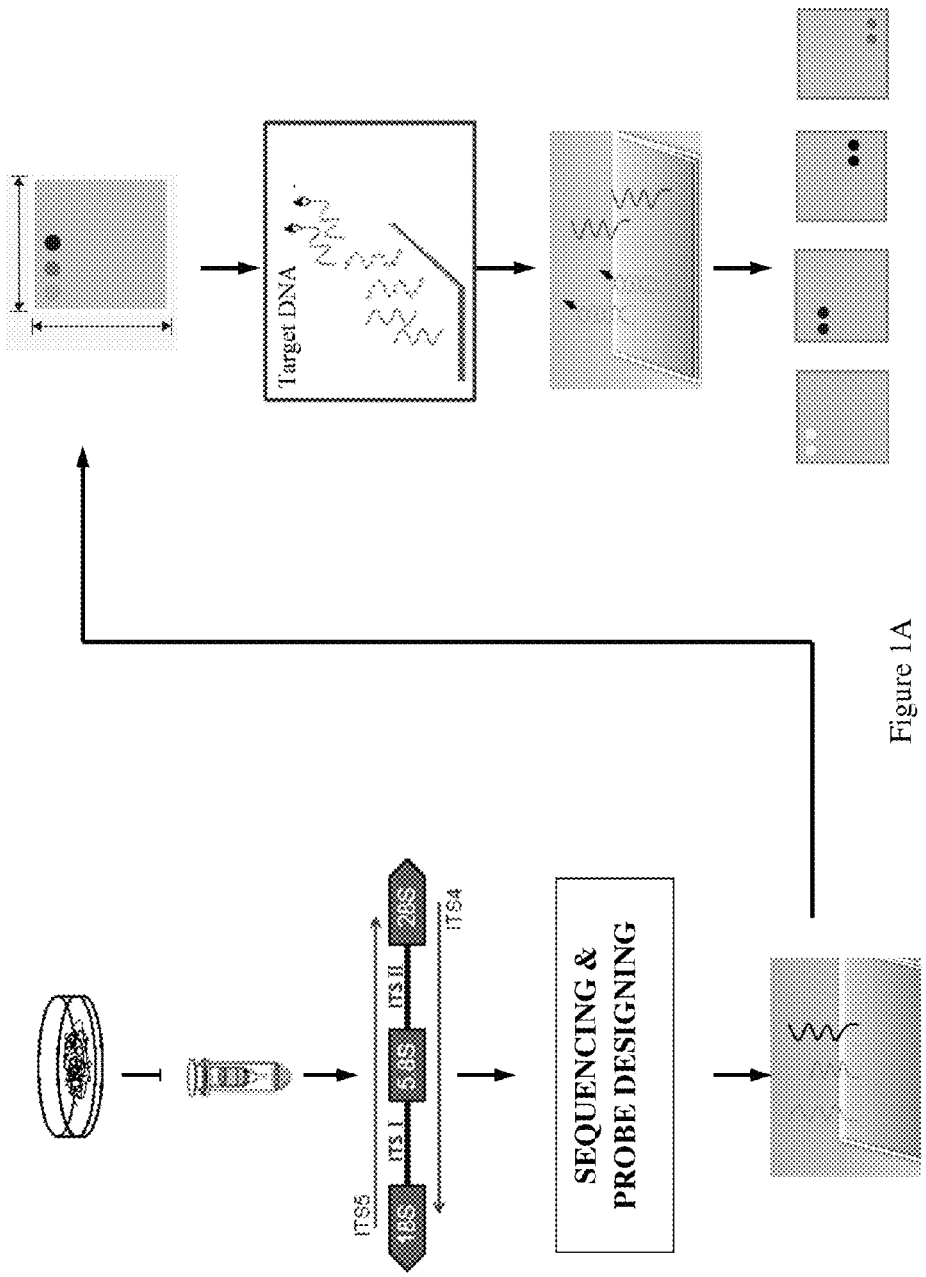
FIG. 1 (A) is a process of constructing the microchip according to the present invention and carrying out the related detection.
FIG. 1(B) is a diagram corresponding to FIG. 1 (A)
Figure 1B:
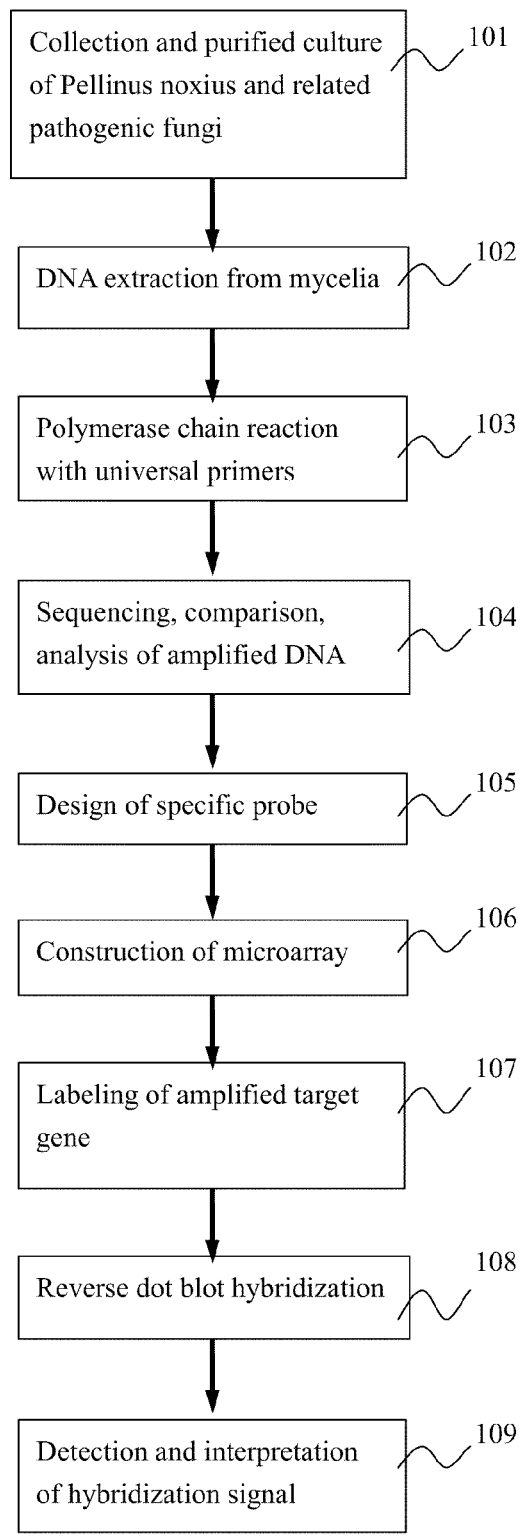

Reference is made to FIGS. 1 (A) and (B). FIG. 1 (A) shows a diagram of designing the probes according to the present invention and constructing and employing the microchip; FIG. 1 (B) shows a process flow diagram corresponding to FIG. 1 (A)

First of all, collection and purified culture of *Phellinus noxius* and related pathogenic fungi were carried out (Step 101).

Fungal Strains for Experiment

The fungal strains used in this embodiment according to the present invention included but were not limited to the seventeen reference strains listed in Table 1. They were all the members of *Phellinus*: *P. apiahynus* (BCRC 35468), *P. cesatii* (BCRC 35431), *P. gilvus* (BCRC 35458), *P. linteus* (TFRI 1100), *P. inrmis* (BCRC 35430), *P. laevigatus* (BCRC 35495), *P. melleoporus* (BCRC 35429), *P. membrance* (BCRC 35411), *P. noxius* (BCRC 35248), *P. pini* (BCRC 35348), *P. quercinus* (BCRC 35352), *P. ribis* (BCRC 35326), *P. formosanus* (TFRI 1129), *P. igniarius* (TFRI 1543), *P. pachyphloens* (TFRI 1131), *P. torulosus* (TFRI 1132), *P. weirii* (FP155613-A-Sp), These important strains of root rot disease (as shown in Table 1) were respectively obtained from Bioresource Collection and Research Center (BCRC, Hsin-Chu, Taiwan), Taiwan Forestry Research Institute (TFRI, Taipei, Taiwan), and USDA Northern Research Station Center for Forest Mycology Research.

TABLE 1

Seventeen strains of *Phellinus* obtained from Bioresource Collection and Research Center (BCRC), Taiwan Forestry Research Institute (TFRI), and USDA Northern Research Station Center for Forest Mycology Research.

| Target Fungi | Source and Strain code |
| --- | --- |
| *Phellinus apiahynus* (Speg.) Rajch. et Wright | BCRC 35468 |
| *Phellinus cesatii* (Bresadola) Ryvarden | BCRC 35431 |
| *Phellinus gilvus* (Schweinitz) Patouillard | BCRC 35458 |
| *Phellinus linteus* | TFRI 1100 |
| *Phellinus inermis* (Ellis: Everh.) Cunningham | BCRC 35430 |
| *Phellinus lavegatus* (Fr. ex Karst.) Bourd. et Galz. | BCRC 35495 |
| *Phellinus melleoporus* (Murrill) Ryvarden | BCRC 35429 |
| *Phellinus membraneceus* Wright et Blument | BCRC 35411 |
| *Phellinus noxius* (Corner) Cunningham | BCRC 35248 |
| *Phellinus pint* (Thore: Fries) Pilat | BCRC 35384 |
| *Phellinus quercinus* Bond, et Ljub. | BCRC 35352 |
| *Phellinus ribis* (Schumacher: Fries) Karsten | BCRC 35326 |
| *Phellinus igniarius* (L.) Quél. | TFRI1129 |
| *Phellinus formosanus* | TFRI543 |
| *Phellinus pachyphloens* | TFRI1131 |
| *Phellinus torulosus* | TFRI1132 |
| *Phellinus weirii* (Murrill) Gilbertson | FP133613-A-SP |

Mycelia Culture

The aforementioned strains were respectively inoculated onto a potato dextrose agar (PDA) plate and then incubated at 26° C. for 7 days. After incubation, the mycelia are scraped off and collected for DNA extraction.

EXAMPLE 2

Amplification and Sequencing of 18S-28S Ribosomal DNA ITS Region

First of all, the mycelia obtained in Step 101 were submitted to mycelia DNA extraction (Step 102), and the method thereof was shown as follows:

About 0.1 g of mycelia was scraped off from a culture plate and placed into an Eppendorf tube 500 µl of CTAB buffer (including 2% CTAB, 1.4M NaCl, 20 mM EDTA, 100 mM Tris (pH 8) and 2% PVP-40) (it is required to preheat at 65° C.) were then added. The mixture was further ground by a tissue grinder. After grinding, 3 µl of 2-mercaptoethanol were added. The mixture was well shaken and mixed and then let stand at 65° C. for 10 to 20 mM 500 µl of CI (chloroform: isoamylalcohol=24:1) were added subsequently and the sample was mixed by gently inverting the Eppendorf tube several times and then centrifuged at 13,200 rpm for 2 min.

After centrifugation, the supernatant (about 500 µl) was transferred to a fresh Eppendorf tube. 300 µl (0.6-fold volume) of isopropanol were added. The sample was then mixed by gently inverting the Eppendorf tube several times to precipitate DNA. The mixture was centrifuged at 13,200 rpm for 2 min After centrifugation, the supernatant was carefully removed. 500 µl of washing buffer (including 76% ethanol and 10 mM ammonium acetate) were added subsequently. The mixture was gently shaken, let stand for 2 min and then centrifuged at 13,200 rpm for 2 min After centrifugation, the supernatant was carefully removed. The residue was then placed into a vacuum-centrifugal dryer (Labconco). After drying out, 200 µl of double-distilled water were added to re-dissolve the residue. It was allowed to add 0.1 µl of RNase to eliminate RNA.

Subsequently, two universal primers were used for the polymerase chain reaction (PCR). These two primers comprised a reverse primer ITS4e (SEQ ID NO: 19) (5'-GCT TAT TGA TAT GCT TAA G-3') and a forward primer ITS5e (SEQ ID NO: 18) (5'-TTA GAG GAA GTA AAA GTC GTA ACA AGG TT-3'). They jointly amplified the sequence of ITS1-5.8S-ITS2 segment from the ribosomal DNA of *Phellinus* according to the present invention. The polymerase chain reaction proceeded as follows: 50 µl of reaction volume (including 35.9 µl of ddH$_2$O, 5 µl of 10× buffer, 1 µl of 10 mM dNTP, 1.5 µl of 10 µM ITS4e primer, 1.5 µl of 10 µM ITS5e primer, 5 µl of template DNA and 1 unit of Taq DNA polymerase) were placed in a PCR reactor (Biometra T3 thermocycler) to undergo the amplification. The reaction temperatures were programmed as follows: i) 94° C. for 4 min, ii) 94° C. for 1 min, iii) 50° C. for 1 min and iv) 72° C. for 2 min (35 cycles) and finally 72° C. for 7 min. In this example, the genomic DNA of *Alternaria alternata* was used as positive control and amplified likewise by the foregoing method. After PCR amplification, the samples were submitted to 1% argarose electrophoresis to make sure whether products from PCR amplification were generated. The PCR products were stored finally at 4° C. and used for DNA sequencing.

PCR products were then purified using an EasyPure PCR Clean Up/Gel Extraction kit (BIOMAN, Scientific Co., Ltd.). The process of purification was carried out as follows: 100 µl of PCR reaction mixture were transferred to a microfuge tube. After addition of 500 µl of PG buffer, the mixture was well shaken and mixed and then transferred to a fresh spin column. After placing the column in a collection tube, the tubes were centrifuged at 6,000 g (8,000 rpm) for 30 sec to remove the filtrate. The spin column was transferred again to a fresh collection tube. To the column, 500 µl of washing buffer were added. The tubes were then centrifuged at 6,000 g (8,000 rpm) for 30 sec to remove the filtrate. The spin column was transferred again to a fresh collection tube. The tubes were then centrifuged at the maximal speed (14,000 rpm) for 2 min. The sample in the column was then allowed to be dried by air. The dried column was then transferred to a fresh microfuge tube and 15 µl of elution buffer or ddH$_2$O were subsequently added to the sample. The tubes were let stand for 2 min so that the elution buffer or ddH$_2$O was absorbed by the sample. The tubes were centrifuged again at the maximal speed (14,000 rpm) for 2 min. The resulted filtrate contained DNA products of the PCR amplification and was stored at −20° C.

Figure 2:
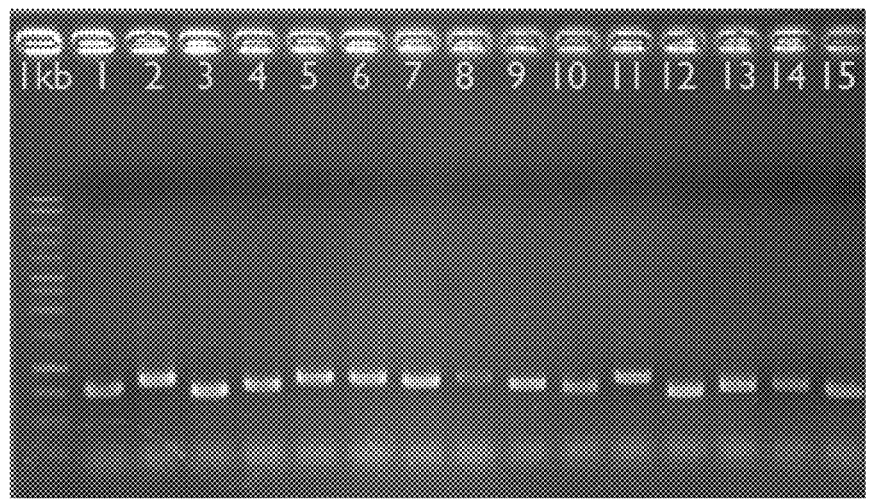
FIG. 2 shows the results of an electrophoresis of PCR products of *Phellinus* species with universal primers.

Reference is made to FIG. 2 that shows the results of an electrophoresis of PCR products of *Phellinus* species with aforementioned universal primers, wherein lanes 1 to 14 respectively corresponds to *P. noxius, P. gilvus, P. laevigatus, P. igniarius, P. robustus, P. longisetulosus, P. melleoporus, P. apiahynus, P. cesatii, P. hoehnelii, P inermis, P. pini, P. quercinus* and *P. ribis*, all of which can obtain DNA products ranging from about 700 to 750 bp PCR amplification. Lane 15 is a positive control which was PCR products from *Alternaria alternata*. In the embodiment of the invention, two universal primers, ITS4 and ITS5, were used to amplify ITS1-5.8S-ITS2 rDNA, the sequence of which includes a small part of 28S posterior segment, ITS1, 5.8S, ITS2 and a small segment of 18S anterior end. Since the size of the ITS segments is very similar and the PCR amplification using universal primers generates products of a single segment, it is quite convenient for sequencing and operation.

Subsequently, the amplified DNA was submitted to sequencing, comparing and analyzing (Step 104), and the method thereof is shown as follows:

DNA Extraction from Gel

The agarose gel was placed on a UV lamp box following electrophoresis. The UV lamp was then switched on and the DNA bands were exhibited on the agarose gel. A piece of gel containing DNA to be purified (approximately 300 mg) was cut out from the gel and placed in a microfuge tube. The amplified DNA was then purified using an aforementioned EasyPure PCR Clean Up/Gel Extraction kit (BIOMAN, Scientific Co., Ltd.). The process was briefly described as follows: 500 µl of PG buffer were added to the gel. The gel and the solution were then well mixed by shaking. The mixture was heated at 55° C. for 5 min During heating, the sample was inverted several times about every two or three minutes until the gel was completely dissolved. 800 µl of the dissolved gel solution were transferred to a spin column. The column was then placed in a collection tube. The tube was centrifuged at 6,000 g (8,000 rpm) for 30 sec to remove the filtrate. The spin column was transferred again to a fresh collection tube. To the column, 500 µl of washing buffer were added. The tube was then centrifuged at 6,000 g (8,000 rpm) for 30 sec to remove the filtrate. The spin column was transferred again to a fresh collection tube. The tube was then centrifuged at the maximal speed (14,000 rpm) for 2 min to dry the sample in the column. The dried column was then transferred to a fresh microfuge tube and 15 µl of elution buffer or ddH$_2$O were subsequently added to the sample. The column was let stand for 2 min so that the elution buffer or ddH$_2$O was absorbed by the sample. The tubes were centrifuged again at the maximal speed (14,000 rpm) for 2 min. The resulted filtrate contained DNA products of the PCR amplification and was stored at −20° C.

EXAMPLE 3

Design of Oligonucleotide Probes

As mentioned above, the EasyPure PCR Clean Up/Gel Extraction kit (BIOMAN, Scientific Co., Ltd.) was employed to purify DNA products directly after the PCR amplification or after gel cutting following electrophoresis. The purified DNA product was then cloned into pGEM-T Easy vector (Promega, WI, USA) and ligated in accordance with the user manual provided by the manufacturer. The ligated product was further transformed into *E. coli* DH5α. Subsequently, the successfully transformed clone was chosen using blue-white colony selection (Sambrook and Russell, 2001) and submitted to the colony PCR for reconfirmation. The clone following confirmation was directly used for sequencing.

Following T-A cloning, the clone underwent sequencing for which an automated DNA sequencer (Applied Biosystems, ABI 3730, Taipei, Taiwan) using BigDye Terminators for fluorescent labeling was employed. Approximately a 1 kb length of each sample automatically interpreted by fluorophotometer in connection with computer could be interpreted, by which the accuracy reached more than 98.5% of the interpretable length.

The sequences resulted from automated sequencing were corrected by using ContigExpress from the Vector NTI 9.0 software package (Infor Max Inc., USA). Next, the nucleotide sequences underwent alignment comparison using AlignX. After comparison of sequences derived from strains of the same species, from diverse species of the same genus or from related species of different genus, specific sequences for *Phellinus* could be designed (Step 105). The design of oligonucleotide probes was carried out by the results of comparison, by which approximately 20 to 60 bp oligonucleotide probes with melting temperature of 55~65° C. could be designed. Then, seven thymine residues were added to the 3' end of the probes to elevate the sensitivity of the probes according to the present invention. In addition, pure related fungal strains were submitted to ITS amplification by PCR using forward primer in combination with the designed universe primer, ITS4, to test the sensitivity and specificity.

The following three points should be noted while designing the probes according to the present invention: i) avoid selecting a sequence with too high GC ratio as probe to eliminate the possibility of nonspecific hybridization, preferably with 40% of GC; ii) avoid selecting a sequence with several successive and identical bases, for example five successive cytosine residues, as probe, and iii) avoid selecting a sequence as probe, which is possible to make the probe to form a secondary structure.

The sequences derived from the fungal strains listed in Table 1 were analyzed with respect to their ITS sequences (including ITS1 and ITS2). After correction of the sequences resulted from automated sequencing by using ContigExpress from the Vector NTI 9.0 software package (Infor Max Inc., USA), the nucleotide sequences then underwent alignment comparison using AlignX. Seventeen specific probes were initially designed for identification of the fungi of *Phellinus*. These seventeen oligonucleotide probes were designated as SEQ ID: 1~17, the sequence and length of which were indicated as shown in Table 2.

TABLE 2

Specific probe sequences derived from *Phellinus*

| Strain designation | Probe code/ SEQ ID NO | Sequence (5' to 3') | Length (bp) |
|---|---|---|---|
| *Phellinus apiahynus* (Speg.) Rajch. et Wright | Phapi/ SEQ ID NO: 1 | GTCTTGTCCCCTCTTTTCATAGGAGGGGGG GGACCAGTCTTTCAAGCTGGTAT | 53 |
| *Phellinus cesatii* (Bresadola) Ryvarden | Phces/ SEQ ID NO: 2 | TAATAGTATTGTGGTGGCCATTTGCTGTTATT CATTGTTAGAAGCGGGTAACC | 53 |
| *Phellinus gilvus* (Schweinitz) Patouillard | Phgil/ SEQ ID NO: 3 | GGATTGAAAGTCGAGGCGCAAGTCTTGA CTGGAGAGAAACCTTTCTACGTTTT | 53 |

TABLE 2-continued

Specific probe sequences derived from *Phellinus*

| Strain designation | Probe code/ SEQ ID NO | Sequence (5' to 3') | Length (bp) |
|---|---|---|---|
| *Phellinus linteus* | Phlin/ SEQ ID NO: 4 | AGAGTCGAAGCTGGAGTAGTCTCTGTAAT CGAAACGGGCTTTTGAAGTATGCT | 53 |
| *Phellinus inermis* (Ellis: Everh.) Cunningham | Phine/ SEQ ID NO: 5 | GTTAGTAAAAGGGGCAAGGAGTAATCCT | 28 |
| *Phellinus lavegatus* (Fr. ex Karst.) Bourd. et Galz. | Phlav/ SEQ ID NO: 6 | TTGGGCGTTTAGGACGGAGTAATGAGTAG AAAGGAGGTGTAATGCTTCCATTT | 53 |
| *Phellinus melleoporus* (Murrill) Ryvarder | Phmel/ SEQ ID NO: 7 | TCAAACTTAACTCGGTTGAAGTGGGGGG AGGAACAGTGCAAGGAGGTGGTGAA | 53 |
| *Phellinus membraneceus* Wright et Blument | Phmem/ SEQ ID NO: 8 | AGGTCGGTGAAAGATATAAGTGTCTCTGA CGCTTGTATTGGAAGCCTTCCTAT | 53 |
| *Phellinus noxius* (Corner) Cunningham | Phnox/ SEQ ID NO: 9 | CTGAAGAGAGAGAGGGAGAGGGAGA GTGGTTTATTCGTTTATTCATTTATTCG | 53 |
| *Phellinus pini* (Thore: Fries) Pilat | Phpin/ SEQ ID NO: 10 | GCCGTCGGGGTTGACTTTGTTAGTAGTGTTT CGACGCGAAAGCATACGGTCGG | 53 |
| *Phellinus quercinus* Bond. et Ljub. | Phque/ SEQ ID NO: 11 | ATTGCTACAAGTATGTTAATAAGGCGAACG CACTCTTTTCGGTGTTACTAGCT | 53 |
| *Phellinus ribis* (Schumacher: Fries) Karsten | Phrib/ SEQ ID NO: 12 | ACGCAAGTGAGTCGTCAGTTCCCCTAAGT TGGGAGTGACTTGATTTGCTTCGT | 53 |
| *Phellinus igniarius* (L.) Quél. | Phign/ SEQ ID NO: 13 | AGTTGGCGGTTAGTAGTCGTAAGGCGAAC ACTTGTCGGCGAACACTTCAATAT | 53 |
| *Phellinus formosanus* | Phfor/ SEQ ID NO: 14 | GGGGCGAGACCTTTGAGTTCGAAGACAGT AGTTCTTTTTGCAAATGTGAGGGC | 53 |
| *Phellinus pachyphloens* | Phpac/ SEQ ID NO: 15 | AATCTCTGGCCATTGGTGTCTTTCATTAGAC GTCGACGTGCCTTTAACTTTGA | 53 |
| *Phellinus torulosus* | Phtor/ SEQ ID NO: 16 | CGTATGTTGGGTCGATGGAAGGTAAAGCTT TACGGCGGCATCTTCTTTAGGTC | 53 |
| *Phellinus weirii* (Murrill) Gilbertson | Phwei/ SEQ ID NO: 17 | GCACTTTTCGAAGTCTGTCGTCGGCTCCCA TTTGGAGCAGCTGGAGGTTT | 50 |

EXAMPLE 4

Construction of Oligonucleotide Microchip

With respect to construction of the microchip (Step 106), a nylon membrane array was used in an embodiment of the present invention. Furthermore, a plastic array was utilized in another embodiment of the present invention. It is still possible to employ other suitable materials for base material of the microchip according to the present invention. The process of the construction is shown as follows:

Preparation of Nylon Membrane Array

Figures 3A, 3B:
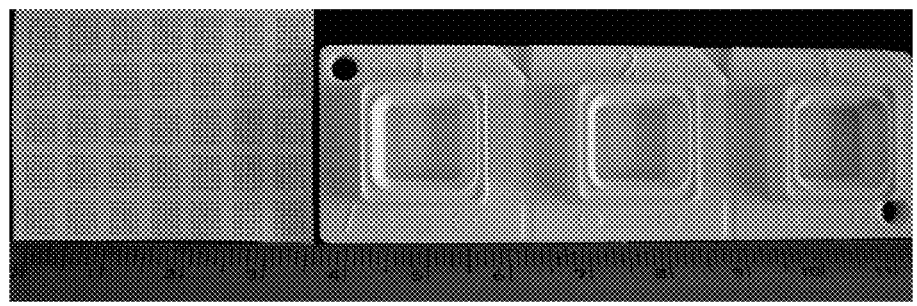
FIG. 3 (A) is a list of position disposition of the probes on the microchip according to the present invention.

A 96-well ELISA plate was prepared. The probes listed in Table 2 of the invention were mixed in equal proportion with microarray tracking dye. Each probe was then transferred to the arranged wells. Each well contained 20 pl of mixture of the probe and the dye (probe : dye=10 μl :10 μl; the final concentration of the probes was 20 μM). Each probe was dotted onto a nylon membrane (positively charged, Roche, Mannheim, Germany) by using a microarrayer, Ezspot™ arrayer RA-300. The position of each oligonucleotide probe on the array was indicated as shown in FIG. 3 (A). The distance between two dot centers was 800 μm. The size of the array was 0.5 cm×0.42 cm and could be provided for 6×5 dots. The dotted and dried nylon membrane was then radiated with UV light of 1.2 J (Stratagene, USA). The real object of finished nylon membrane array was indicated as shown in FIG. 3(B), left, wherein the position of the probes from upper left to lower right, respectively corresponded to *P. apiahynus* (Phapi), *P. cesatii* (Phces), *P. gilvus* (Phgil), *P. linteus* (Phlin), *P. inrmis* (Phinr), *P. laevigatus* (Phlae), *P. melleoporus* (Phmel), *P. membrance* (Phmem), *P. noxius* (Phnox), *P. pini* (Phpin), *P. quercinus* (Phque), *P. ribis* (Phrib), *P. formosanus* (Phfor), *P. igniarius* (Phign), *P. pachyphloens* (Phpac), *P. torulosus* (Phtor) and *P. weirii* (Phwei). In addition, this array still included a positive control (PC), a hybridization control (HC), a negative control (NC) and a position marker (PM). The probe for positive control was a highly conservative 5.8S fragment, the sequence of which was 5'-ATTCACTGAAT-TCTGCAATTCACATTACTTATCG-CATTTCGCTGCGTTCTTCATCGATGC-3' (SEQ ID NO: 20). The probe for hybridization control was a KS domain gene fragment of Colletotrichum graminicola, the sequence of which was 5'-GCTGTCATTTTGGGTACTGCCAC-CAACCACTCTGCCGATGCCATCTCCATCACCC-3'

(SEQ ID NO: 21). The negative control was sterilized ddH$_2$O. The position marker was oligo-(dT)$_{10}$ labeled labeled with digoxigenin or biotin at the 5' end.

Preparation of Plastic Array

The probe was mixed in equal proportion with probe buffer (DR. Chip Biotech. Inc., Hsinchu, Taiwan) and the final concentration of the probe was 20 μM. The DR. Chip Biotech. Inc (Hsinchu, Taiwan) was commissioned to dot the prepared probes and the dotted microchip could be employed immediately. The positions of the probes and the controls were fully identical to those of the nylon membrane array. The real object of finished plastic array was indicated as shown in FIG. 3(B), right.

EXAMPLE 5

Hybridization of Oligonucleotide Microchip

1. DNA Extraction from Wood Specimens

A small piece of infected wood tissue was scraped off and liquid nitrogen was then added. Next, the frozen specimen was ground to powder. Then, 0.1 g of the powder was weighed into a microfuge tube. 500 μl of CTAB buffer (it is required to preheat at 65° C.) were then added. The mixture was further ground by a tissue grinder. After grinding, 3 μl of 2-mercaptoethanol were added. The mixture was well shaken and mixed and then let stand at 65° C. for 10 to 20 min 500 μl of CI (chloroform:isoamylalcohol=24:1) were added subsequently and the sample was mixed by gently inverting the Eppendorf tube several times and then centrifuged at 13,200 rpm for 2 min. After centrifugation, the supernatant (about 500 μl) was transferred to a fresh Eppendorf cup. 300 μl (0.6-fold volume) of isopropanol were added. The sample was then mixed by gently inverting the Eppendorf tube several times to precipitate DNA. The mixture was centrifuged at 13,200 rpm for 2 min. After centrifugation, the supernatant was carefully decanted (into a waste tank). 500 μl of washing buffer were added subsequently. The mixture was gently shaken, let stand for 2 min and then centrifuged at 13,200 rpm for 2 min. After centrifugation, the supernatant was carefully removed. The residue was then placed into a vacuum-centrifugal dryer (Labconco). After drying out, 200 μl of double-distilled water were added to re-dissolve the residue (it was allowed to add 0.1 μl of RNase to eliminate RNA).

2. DNA ITS Segment (ITS1-5.8S-ITS2 rDNA Segment) of the Aforementioned Sample Infected Fungal Strain to be Tested Prior to Amplification (Step 107)

While amplifying ITS segment, the primers used were a forward primer (ITS5e) and a reverse primer (ITS 4e) and digoxin (DIG) or biotin was labeled at 5' end of the primers. The conditions for the PCR have been described in Step 103 and will be not further stated any more.

3. Reverse Dot Blot Hybridization (Step 108)

(i) Hybridization of Nylon Membrane Array

To each nylon membrane array, 0.5×SSC [1×SSC contains 0.15 M sodium chloride, 0.015 M sodium citrate (pH 7.0) and 0.1% sodium dodecyl sulfate (SDS)] was added. The arrays were rinsed twice at room temperature (shaken on the orbital shaker at 75 rpm) for 2 min each time to remove the microarray tracking dye. Then, 5 μl of target DNA resulted from amplification of forest fungal strain to be tested by PCR and 2 μl of PCR product of *Colletotrichum graminicola* KS domain as hybridization control were simultaneously added to 200 μl of hybridization solution [5×SSC, 1% (w/v) blocking reagent (Roche), 0.1% N-laurylsarcosine (Sigma) and 0.02% SDS]. The mixture was then heated at 95° C. for 6 min to denature DNA, whereby the double-stranded DNA was unwound to form two single-stranded DNA. The mixture was placed on the ice to keep DNA in single-stranded form. Subsequently, the microchips and the denatured products were added to a 24-well culture plate (Technp Plastic Products, Trasadingen, Switzerland) and then the plate was placed in a hybridization incubator, where the hybridization was carried out at 50° C. and 120 rpm for 2 hr. After hybridization, the nylon membrane arrays were rinsed with 0.25×SSC-0.1% SDS buffer at 58° C. four times (5 min each time) to remove residual probes. Next, an alkaline phosphatase-conjugated anti-digoxigenin-AP Fab fragments (Roche, Germany) diluted 2,500-fold with 1% (w/v) blocking reagent dissolved in maleic acid buffer [0.1M maleic acid (Sigma) and 0.15 M NaCl] (against digoxigenin-labeled DNA) or a Streptavidin-AP diluted 1,000-fold with the foregoing blocking reagent was added to the arrays. The arrays were let stand at room temperature for 1 hr (Dig system) or 30 min (biotin system). After reaction, 200 μl of MAB Wash Buffer (0.3% (v/v) Tween 20 in maleic acid buffer) were added. The arrays were washed twice (15 min each time) to remove non-conjugated antibody or Streptavidin-AP. After washing, 200 μl of detection buffer (including 0.1 M Tris-HCl and 0.15 M NaCl, pH 9.5) were added. The arrays were rinsed at room temperature for 1 min. Then, the detection buffer was removed again. Subsequently, NBT/BCIP (nitroblue tetrazolium chloride/5-bromo-4-chloro-3-indolylphosphate, Roche) was diluted 50-fold with the foregoing detection buffer and mixed well. To each well of a 24-well culture plate, the foregoing nylon membrane arrays were added and then 100 μl of NBT/BCIP mixture were dropwise added. The reaction was then carried out in dark at room temperature for 30 min. The reaction mixture could not be shaken during the reaction. After the color reaction, the arrays were rinsed with the sterilized water four times to remove residual NBT/BCIP from the nylon membrane. After color appeared, the nylon membrane arrays were placed on a filter paper and then transferred into an oven. Finally, the dried nylon membrane arrays were scanned by a scanner, Umax powerlook 3000 (Taipei, Taiwan) with high resolution (3,000 dpi) and the image of the hybridization was then saved.

(ii) Hybridization of Plastic Array

4 μl of target DNA resulted from amplification of forest fungal strain to be tested by PCR and 2 μl of PCR product of *Colletotrichum graminicola* KS domain as hybridization control were simultaneously added to 220 μl of hybridization solution. The mixture was then heated at 95° C. for 6 min to denature DNA, whereby the double-stranded DNA was unwound to form two single-stranded DNA. The mixture was immediately placed on the ice to keep DNA in single-stranded form and then added to the plastic arrays dotted by the DR. Chip Biotech. Inc (Hsinchu, Taiwan). After the addition, the arrays were placed into a small oven [Dr. Mini Oven (DR. Chip Biotech. Inc, Hsinchu, Taiwan)], where hybridization reaction was carried out at the highest rotation speed at 50° C. for 1 hr. After hybridization, the arrays were washed in oven at 58° C. with 220 μl of 0.25×SSC four times (5 min each time) to remove residual probes. Next, an alkaline phosphatase-conjugated anti-digoxigenin-AP Fab fragments (Roche, Germany) diluted 2,500-fold with blocking reagent (against digoxigenin-labeled DNA) or a Streptavidin-AP diluted 1,000-fold with the foregoing blocking reagent was added to the arrays. The arrays were let stand at room temperature for 1 hr (Dig system) or 30 min (biotin system). After reaction, 200 μl of MAB Wash Buffer were added. The arrays were washed twice (15 min each time) to remove non-conjugated antibody or Streptavidin-AP. After washing, 200 μl of detection buffer were added. The arrays were rinsed at room temperature for 1 min. Then, the detection buffer was removed again. Subsequently, NBT/BCIP (nitroblue tetrazolium chloride/5-bromo-4-chloro-3-indolylphosphate, Roche) was diluted 50-fold with the foregoing detection buffer and mixed well. To each array, 100 µl of NBT/BCIP mixture were dropwise added. The reaction was then carried out in dark at room temperature for 30 min. The reaction mixture could not be shaken during the reaction. After the color reaction, the arrays were rinsed with the sterilized water four times to remove residual NBT/BCIP from the nylon membrane. After color appeared, the nylon membrane arrays were dried out in an oven.

4. Detection of Hybridization Signal (Step 109)

Figure 4:
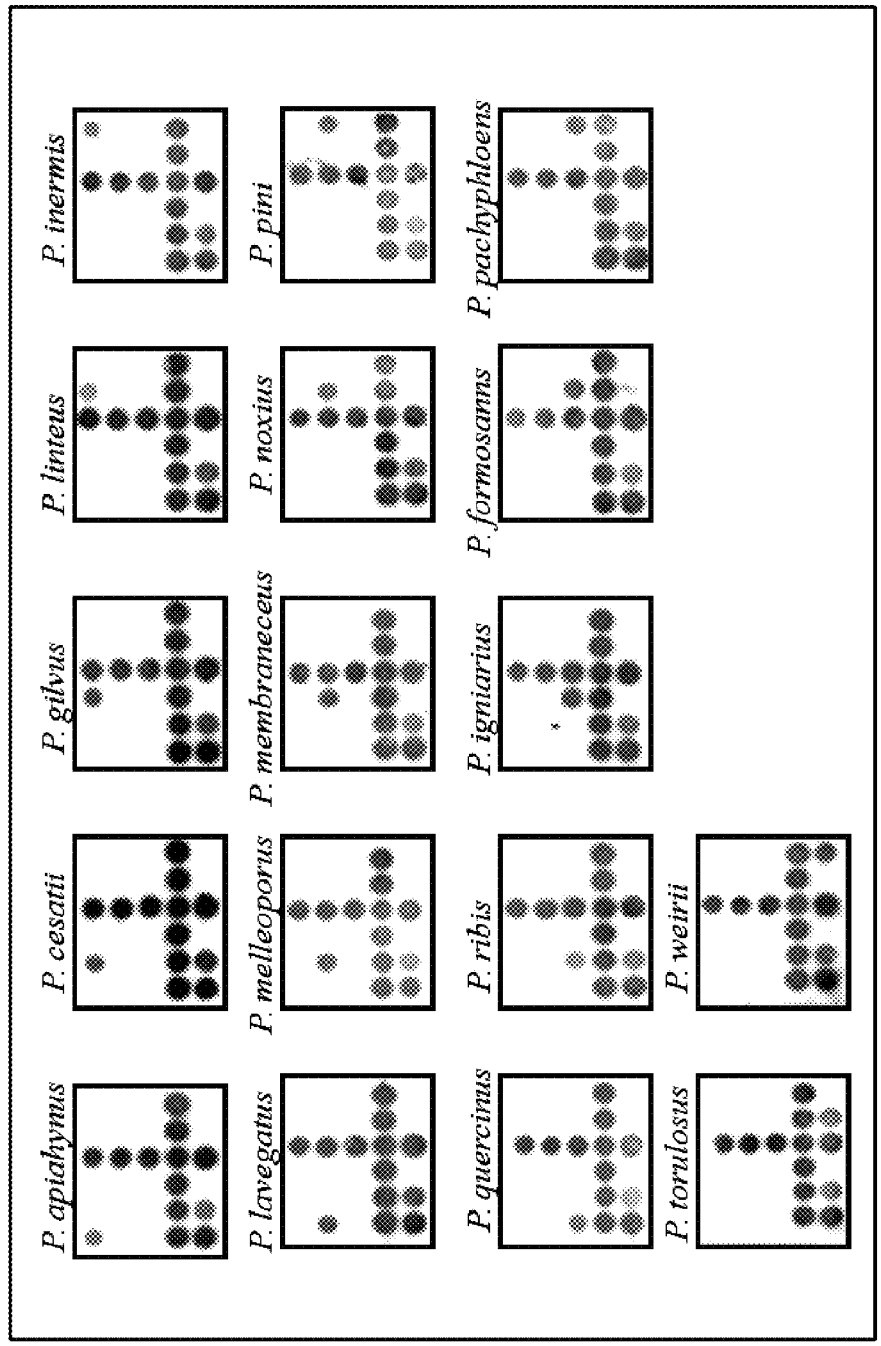
FIG. 4 shows the results of hybridization with respect to the nylon membrane array.
Figure 5:
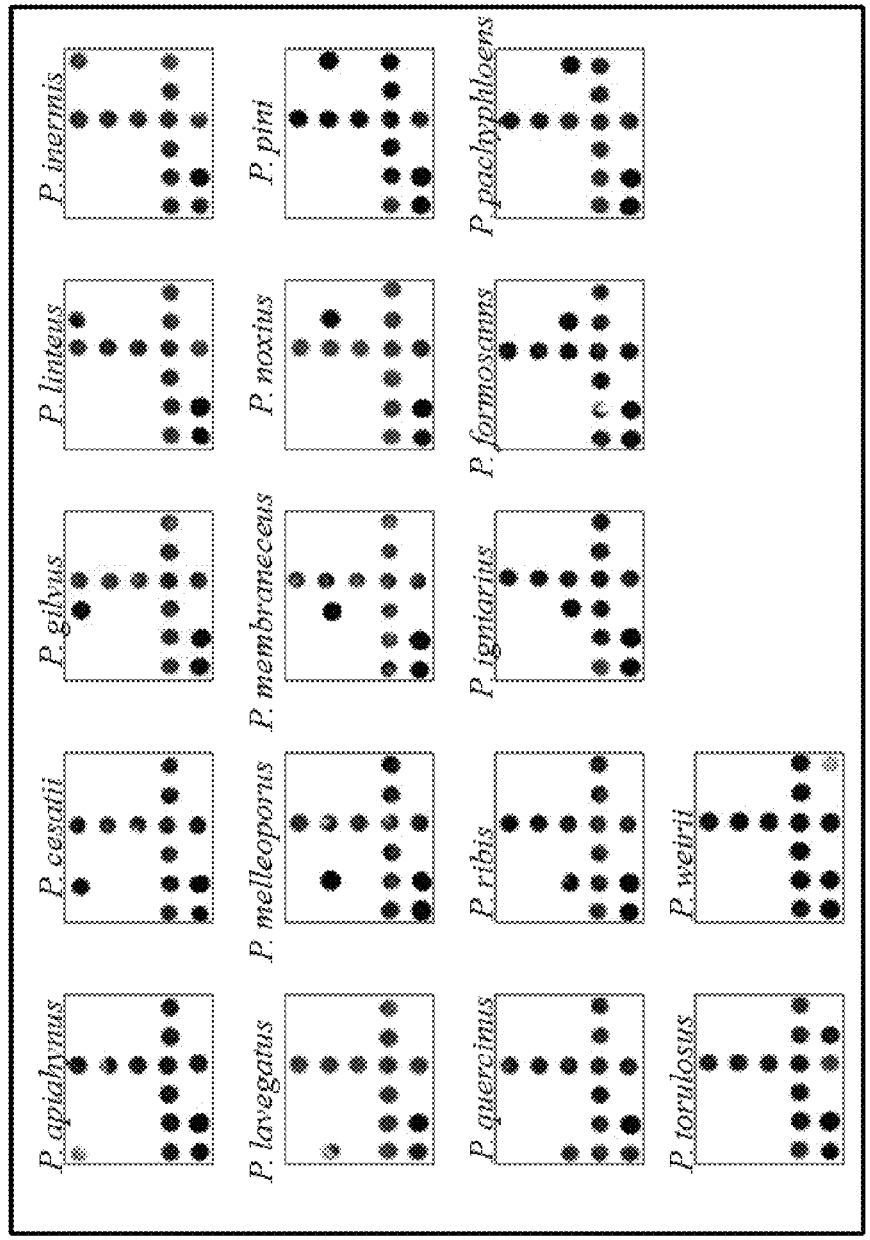
FIG. 5 shows the results of hybridization with respect to the plastic array.

The results on hybridization with nylon membrane array/plastic array can be directly interpreted visually. The position marker on the array can separate the nylon membrane into four regions that are positions capable of showing color reaction signal resulted from hybridization and interpreting the reacted probes. The reaction between the positive control (PC) and hybridization control (HC) must take place. This means the overall reaction is effective. In contrast, the negative control (NC) shall be colorless. This implies no false positive reaction occurs.

Wherein with respect to the results of hybridization with the nylon membrane array, the reference is made to FIG. 4, and with respect to the results of hybridization with the plastic array, the reference is made to FIG. 5. Whether a nylon membrane array or a plastic array was used, it was capable of exhibiting specific signals for the seventeen fungal species of *Phellinus*. The arrays could be directly labeled with the position marker and the species of the detected fungi could be identified by the exhibited signals. Furthermore, it could be seen from the results of hybridaization that the nylon membrane array showed higher background values and easily formed dirts. Moreover, the nylon membrane array required much longer time for hybridization. In contrast, the plastic array exhibited much more explicit reaction results and seldom formed background values and dirts. In addition, the reaction time of this array was faster than that of the nylon membrane array by more than 1 hour.

EXAMPLE 6

Test on the Sensitivity of the Microchip

Figure 6A:
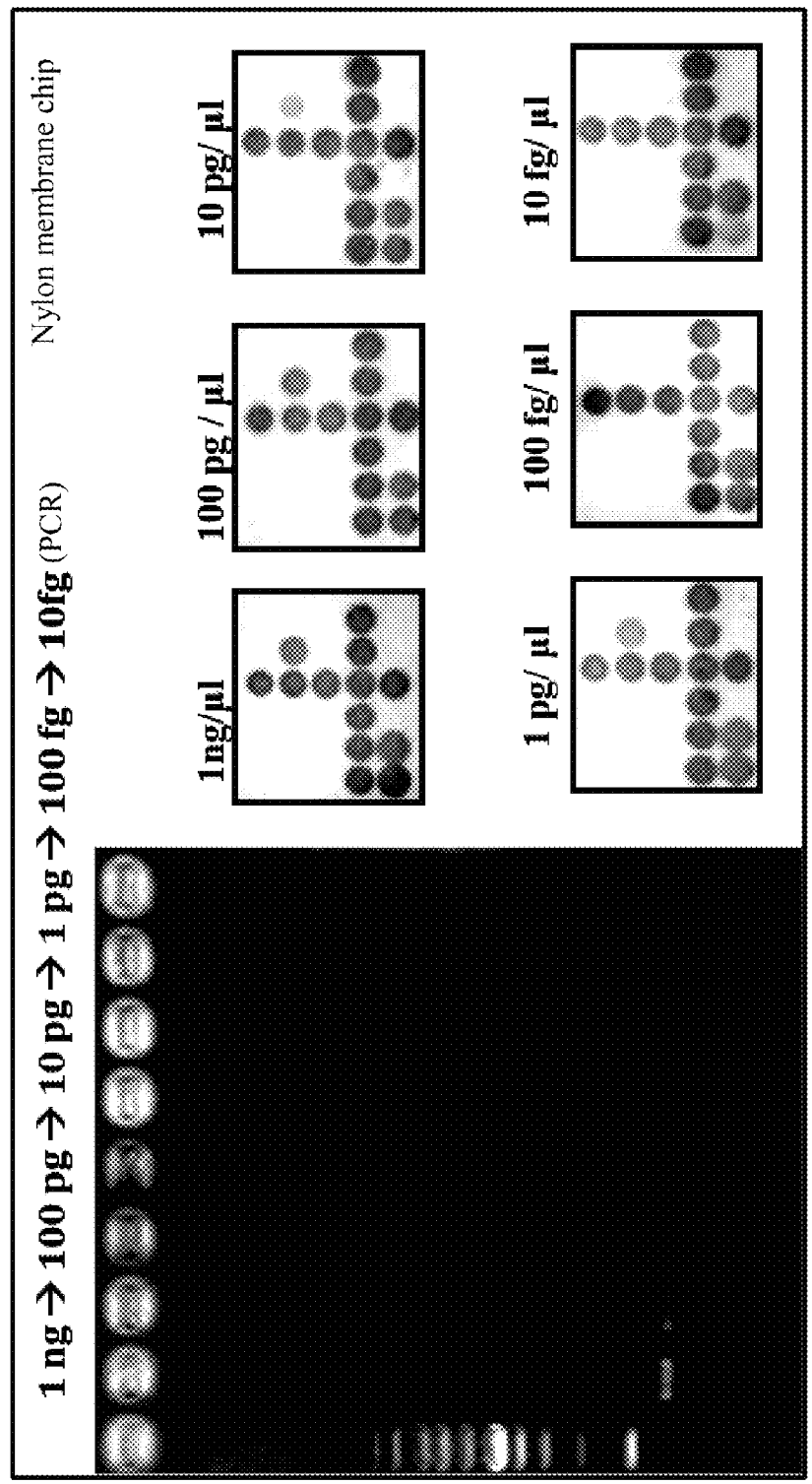
FIG. 6 (A) shows the test results on the sensitivity of the probes with respect to the nylon membrane array, in comparing the sensitivity in gel in PCR.
Figure 6B:
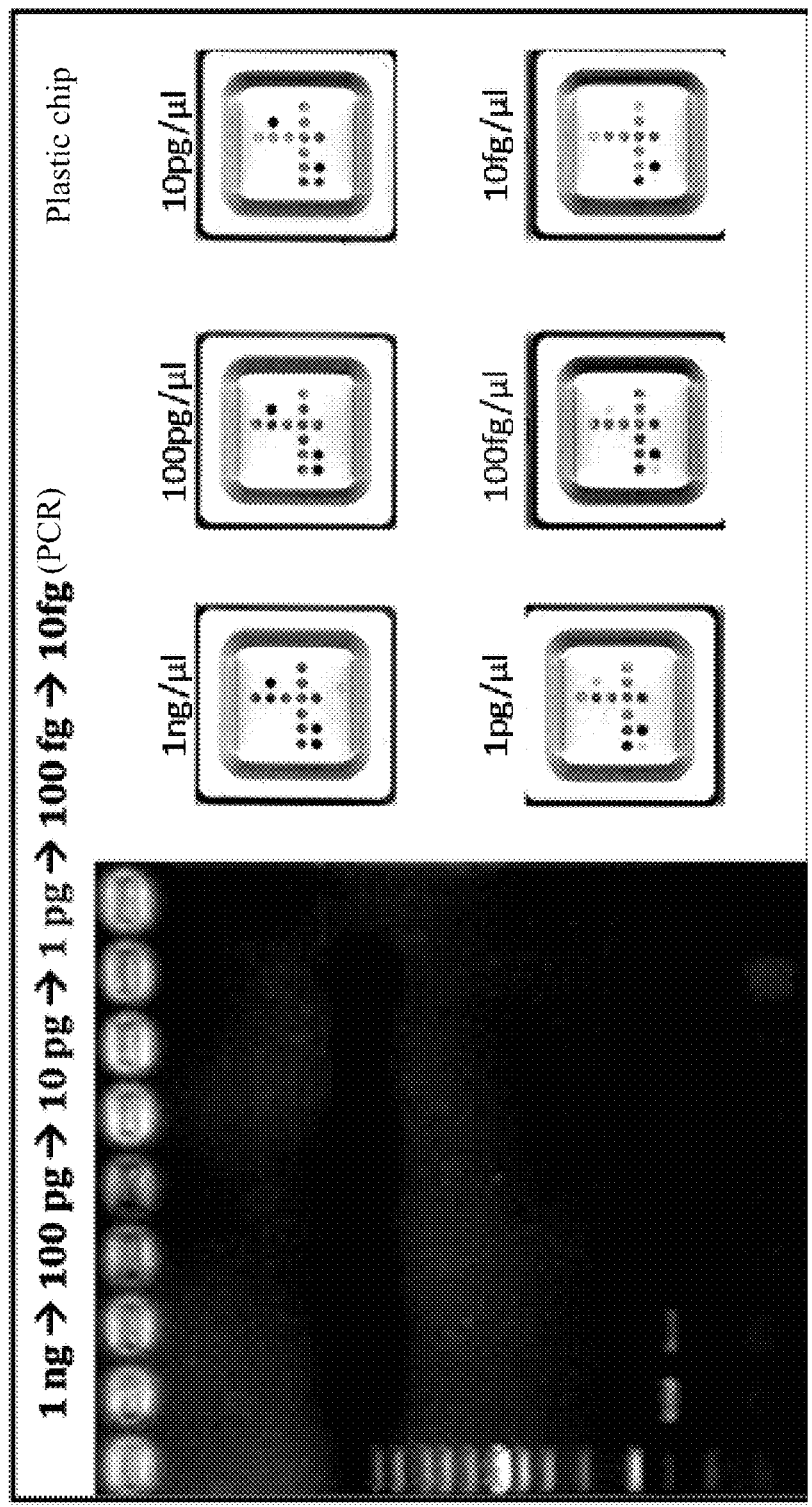

Reference is made to FIGS. 6 (A) and (B). FIG. 6 (A) showed the test results on the sensitivity of the probes with respect to the nylon membrane array; FIG. 6 (B) showed the test results on the sensitivity of the probes with respect to the plastic array. First, DNA extracted from *Phellinus noxius* was diluted serially (the resulted DNA concentrations were 1 ng/µl, 100 pg/µl, 10 pg/µl, 1 pg/µl, 100 fg/µl and 10 fg/µl, respectively). Next, the serially diluted DNA samples were amplified by PCR using universal primers [see FIGS. (A) and (B), left side, electrophoretogram]. Subsequently, the target DNA resulted from amplification of the serially diluted DNA samples by PCR was hybridized with the specific probes dotted on the nylon membrane array or the plastic array [see FIGS. 6 (A) and (B); (A) nylon membrane array; (b) plastic array]. The results showed the sensitivity with which ITS products could be detected by PCR was 10 pg/µl, whereas the sensitivities of the nylon membrane array and the plastic arrays were respectively 1 pg/µl and 100 fg/µl. Therefore, it was obvious the sensitivity of the microchip was better than that of PCR.

EXAMPLE 7

Figure 7:
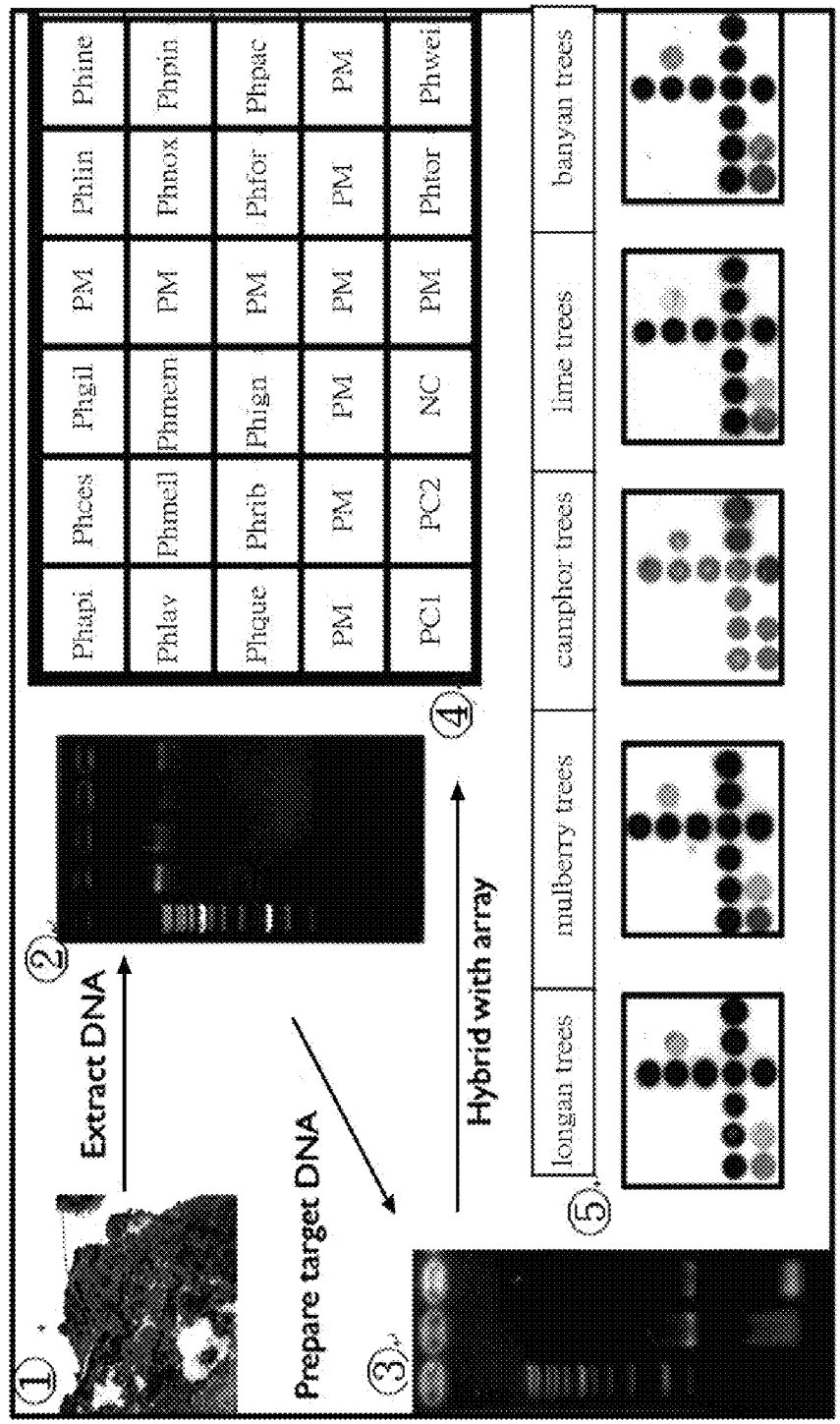
FIG. 7 shows the detection results on diverse suspected infected wood tissues with the microchip according to the present invention.

Detection and Identification of the Fungal Pathogens of Infected Wood Specimens Using the Microchip 1. Detection Results on Diverse Suspected Infected Wood Tissues with the Microchip According to the Present Invention (See FIG. 7).

First, a CTAB-Mini DNA extraction kit was used to extract DNA from the wood tissues (longan trees, mulberry trees, camphor trees, lime trees and banyan trees) suspected to be infected by root rot disease reported by Taiwan Forestry Research Institute. Next, the PCR was immediately carried out to amplify the target DNA from the extracted DNA samples. Since the extracted DNA samples contained DNA derived from the plants and other fungi and bacteria, a faint smear would be generated following PCR. It was expected to form a specific fragment for approximately 700 bp. Subsequently, the PCR products were hybridized with *Phellinus*' array. The hybridization resulted in specific signal. The position of the signal was conformed to the expected *Phellinus noxius*. The result demonstrated the wilting of the forests was caused by *Phellinus noxius*. Since the identification process of the example could be accomplished within seven hours, so the method had good time-effectiveness.

2. Confirmation of the Specificity of the Detection Results of the Microchip According to the Invention The PCR amplification products of infected wood tissues were sequenced. The sequences were then compared with those in the NCBI's GenBank. The results were indicated in table 3. To make sure the signal generated by hybridizing with the microchip according to the present invention was correct, DNA was extracted from the foregoing isolated fungus that was identified as *Phellinus noxius* by the microchip according to the present invention. Then, the extracted DNA underwent PCR amplification with universal primers. After PCR, the amplified product was sequenced and underwent T-A cloning. The resulted product was further assigned to a biotechnology company for DNA sequencing. The sequence obtained was then submitted for BLAST comparison in the NCBI's GenBank. The sequence of *Phellinus noxius* did not emerge because the database of the NCBI's GenBank has not saved the sequence of *Phellinus noxius* so far. However, a number of fungal species in close relationship (for example *Inonotus pachyphloeus, Phellinus laeviqatus, Fuscoporia cinchoensis* and *Pseudochaete tabacina*) could be found. Due to high e-values and similarity, the pathogen of the infected wood specimens was deduced to be *Phellinus noxius*.

TABLE 3

| BLAST results (NCBI GenBank Database Center) | | | | | | |
|---|---|---|---|---|---|---|
| Accession | Description | Max score | Total Score | Query coverage | E value | Max ident |
| AY558635.1 | *Inontus pachyphloeus* strain CBS 193.37 internal transcribed spacer | <u>560</u> | 560 | 72% | 2e−156 | 89% |

TABLE 3-continued

BLAST results (NCBI GenBank Database Center)

| Accession | Description | Max score | Total Score | Query coverage | E value | Max ident |
|---|---|---|---|---|---|---|
| AY340053.1 | *Phellinus leaviqatus* strain 89-119 18S ribosomal RNA gene, partial se | 342 | 342 | 58% | 9e–91 | 83% |
| AY558613.1 | *Fuscoporia cinchonensis* strain CBS 447.76 internal transcribed spacer | 337 | 337 | 52% | 4e–89 | 85% |
| AY558598.1 | *Pseudochaete tabacina* straun IFO 4969 internal transcribed spacer 1, | 337 | 337 | 73% | 4e–89 | 80% |
| AF053226.1 | *Phellinus leaviqatus* 18S ribosomal RNA gene, partial sequence; intern | 329 | 329 | 59% | 7e–87 | 83% |
| AY558626.1 | *Phellinus leaviqatus* strain CFMR 5640 internal transcribed spacer 1, 5 | 326 | 326 | 58% | 9e–86 | 83% |

Figure 8B:
FIG. 8 shows the feature of the colony (A) and microscopic characters (B) of the suspected fungal pathogens isolated from the *Phellinus noxius* infected specimens of the woods, which comply the circumscription of previously described *Phellinus noxius.*
Figure 8A:
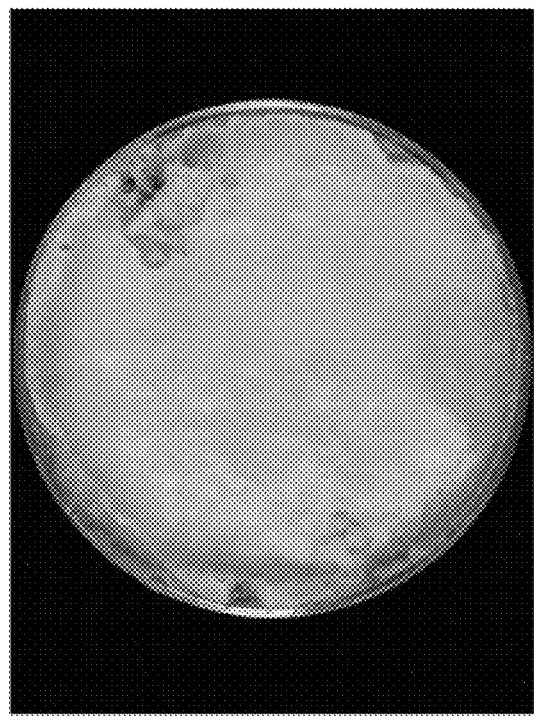

3. Confirmation of the Identification Results of the Microchip According to the Invention by Tissue Culture Reference is made to FIG. 8 (A) and (B) that respectively showed the isolation and culture of pathogenic fungi from infected specimens of the woods and the results of morphological identification. To make sure the detection results of the microchip once again, an infected wood tissue (longan trees, mulberry trees, camphor trees, lime trees and banyan trees) was sterilized with 10% sodium hypochlorite. Next, the tissue was cut up and a small piece of tissue was picked and placed onto the potato dextrose agar (PDA). The incubation was carried out at 25° C. It can be seen in FIG. 8 (A) that the mycelia grew to reach confluence following incubation for 5 days and there brown mycelia presented in the culture. The mycelia were subsequently examined under compound light microscope. In FIG. 8 (B), antler-shaped mycelia (trocyst) formed by the extension of the mycelia could be observed. This is the unique structural characteristic of *Phellinus noxius*, which was perfectly consistent with the identification results obtained by the microchip. It is therefore demonstrated this array can be used to identify and detect specific pathogenic fungi.

From the foregoing examples, it is apparent that the use of the differences in the nuclear ITS gene sequences of *Phellinus* genus, design of specific probes and construction of the nylon membrane array or the plastic array can precisely, rapidly and simultaneously detect and identify seventeen fungi of *Phellinus*, including softwood and hardwood killer, *Phellinus noxius* and *Phellinus weirii*. The microchips according to the present invention can provide nursery and seedlings early diagnosis, detection and certification, and for the affiliation of domestic and foreign custom inspection and quarantine, including coniferous trees, broad leaf trees and seedlings. And also can be used in ecology monitoring, silviculture management and policy making.

The embodiments of the present invention has been detailed based on examples and attached figures. However, the persons skilled in the art may, if necessary, modify or alter the invention without departing from the spirit and scope of the invention. Therefore, the definition with respect to the scope of the invention refers to the claims of the invention.

What is claimed is:

1. A microchip for identifying *Phellinus* species, comprising:
   a substrate; and
   seventeen DNA probes immobilized on the substrate,
   wherein the DNA probes consists of sequences SEQ ID NOs: 1-17, or the seventeen complement sequences of SEQ ID NOs: 1-17.

2. The microchip for identifying *Phellinus* species as claimed in claim 1, wherein the substrate is a nylon membrane.

3. The microchip for identifying *Phellinus* species as claimed in claim 1, wherein the substrate is a plastic material.

4. The microchip for identifying *Phellinus* species as claimed in claim 1 further comprising a position marker.

5. The microchip for identifying *Phellinus* species as claimed in claim 4, wherein the position marker is oligo-(dT)$_{10}$ labeled with digoxigenin or biotin at the 5' end.

6. A method of identifying a *Phellinus* species, comprising:
   (a) extracting DNA from a sample;
   (b) amplifying an internal transcribed spacer (ITS) of a 18S-28S rDNA gene of the extracted DNA to obtain an amplification product;
   (c) hybridizing the amplification product with the microchip as claimed in claim 1; and
   (d) determining whether the amplification product detectably hybridize to the DNA probes of the microchip.

7. The method of identifying a *Phellinus* species as claimed claim 6, wherein the substrate of the microchip is a nylon membrane.

8. The method of identifying a *Phellinus* species as claimed in claim 6, wherein the substrate of the microchip is a plastic material.

9. The method of identifying a *Phellinus* species as claimed in claim 6, wherein the microchip further comprises a position marker.

10. The method of identifying a *Phellinus* species as claimed in claim 9, wherein the position marker is oligo-(dT)$_{10}$ labeled with digoxigenin or biotin at the 5' end.

11. The method of identifying a *Phellinus* species as claimed in claim 6, wherein (b) further comprises a step of performing an electrophoresis to confirm the presence of the amplification product.

12. The method of identifying a *Phellinus* species as claimed in claim 6, wherein a forward primer having the sequence of SEQ ID NO: 18 and a reverse primer having the sequence of SEQ ID NO: 19 are used for amplification (b).

13. The method of identifying a *Phellinus* species as claimed in claim 12, wherein the forward primer and reverse primer used in (b) are labeled with digoxigenin (DIG).

14. The method of identifying a *Phellinus* species as claimed in claim 12, wherein the forward primer and reverse primer used in (b) are labeled with biotin.

15. A probe composition for identifying *Phellinus* species, said probe composition consisting of seventeen DNA probes, wherein the sequences of the seventeen DNA probes consist of sequences SEQ ID NOs: 1-17, or the seventeen complement sequences of SEQ ID NOs: 1-17, and wherein one or more of said DNA probes is labeled with digoxgenin (DIG) or biotin.

* * * * *